United States Patent

Orzi et al.

[11] Patent Number: 5,241,090
[45] Date of Patent: Aug. 31, 1993

[54] PROCESS FOR THE PREPARATION OF 4-AMINO-UNSATURATED ANDROSTANEDIONE DERIVATIVES

[75] Inventors: Fabrizio Orzi; Antonio Longo, both of Milan; Matteo D'Anello, Cormano; Natale Barbugian, Milan, all of Italy

[73] Assignee: Farmitalia Carlo Erba S.R.L., Milan, Italy

[21] Appl. No.: 885,856

[22] Filed: May 20, 1992

[30] Foreign Application Priority Data

May 24, 1991 [GB] United Kingdom ............... 9111260

[51] Int. Cl.$^5$ ............ C07J 41/00; C07J 71/00
[52] U.S. Cl. ........................ 552/515; 540/81
[58] Field of Search ............ 552/515; 540/81; 514/177

[56] References Cited

U.S. PATENT DOCUMENTS 4,757,061 7/1988 Faustini et al. ............... 514/177
4,865,766 9/1989 Longo et al. ............... 514/177

*Primary Examiner*—Marianne M. Cintins
*Assistant Examiner*—Kimberly J. Kestler
*Attorney, Agent, or Firm*—Oblon, Spivak, McClelland, Maier & Neustadt

[57] ABSTRACT

4-amino-unsaturated androstanedione derivatives provided with aromatase inhibitory activity are obtained by hydrolyzation of a corresponding compound of formula II

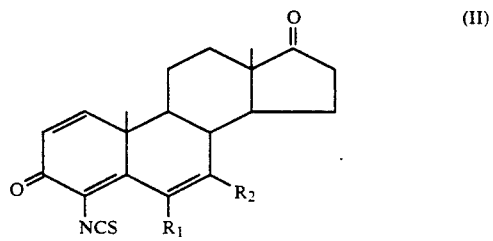

6 Claims, No Drawings

PROCESS FOR THE PREPARATION OF 4-AMINO-UNSATURATED ANDROSTANEDIONE DERIVATIVES

The present invention relates to a new process for the preparation of 4-amino-unsaturated androstanedione derivatives, in particular 4-aminoandrosta-1,4,6-triene-3,17-diones, having valuable aromatase inhibitory activity.

The 4-aminoandrosta-1,4,6-triene-3,17-diones, which can be prepared by the new process of the present invention, are known from U.S. Pat. No. 4,757,061. According to this U.S. patent, these compounds can be obtained by reacting a suitable androsta-1,4-diene-3,17-dione derivative with a compound of formula $M-N_3$, wherein M is an alkali metal or ammonium cation, or a tri-$C_1$-$C_6$ alkylsilyl group, so obtaining a 4-azido-androsta-1,4,6-triene-3,17-dione derivative, which is then reduced to obtain the corresponding 4-amino derivative. U.S. Pat. No. 4,757,061 provides all the details of the reactions concerned: a preferred compound of formula $M-N_3$ is sodium azide.

By duly considering the process for preparing the 4-amino-derivatives, described in U.S. Pat. No. 4,757,061, it appears clear that a skilled chemist can safely carry out in laboratory all the chemical reactions involved in such process.

Indeed, even if reagents like sodium azide are used, they are only in very small amounts, namely not hazardous amounts, that can be safely handled.

However, when the above-mentioned process is transferred from the laboratory small-scale to the industrial large-scale production, the presence of large amounts of azothydric acid and working intermediate organic azido-compounds at high temperature may involve risks.

These risks, which are mainly of environmental and healthy nature, can be safely avoided by using a chemical plant specifically built for such process. However, a plant having these characteristics is unlikely to be re-converted to fit different chemical processes and this is not in agreement with the requirements of a good industrial economy.

From the above it appears clear that the process provided by U.S. Pat. No. 4,757,061, although being a good process, involves high costs. Therefore there is the need of different processes which provide such 4-aminoandrosta-1,4,6-triene-3,17-diones, but avoid the above drawbacks.

This has been reached for instance by the process provided by U.S. Pat. No. 4,865,776. Accordingly, the desired 4-amino-unsaturated androstenediones are obtained by a process comprising, in particular, the reaction of a suitable 4-haloandrosta-1,4,6-triene-3,17-dione derivative with ammonia. Given that the process according to U.S. Pat. No. 4,865,776 avoids using sodium azide, the end-products are obtained at lower costs, even if the yields provided by this process are in general slightly lower than those provided by the previous process according to U.S. Pat. No. 4,757,061.

We have now found a new process which, besides avoiding the use of azido compounds, provides the desired 4-aminoandrosta-1,4,6-triene-3,17-dione derivatives in higher yields than those provided by the previous process according to U.S. Pat. No. 4,865,776. In fact, in the implementation of the process described in U.S. Pat. No. 4,865,776 for the laboratory scale production, e.g. of the compound 4-aminoandrosta-1,4,6-triene-3,17-dione, a yield of about 10% is obtained, whereas the pilot scale production of the same compound by the new process of the present invention, starting from the same intermediate compound, provides a yield of about 15%. Since this yield increase has been reached in the large-scale production, it makes the new process according to the present invention of particular value.

Accordingly, the present invention relates to a new process for the preparation of 4-amino-androstanedione derivatives having the following formula (I), and the pharmaceutically acceptable salts thereof.

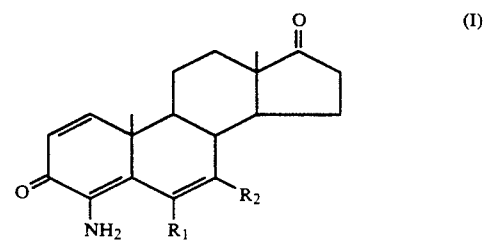

wherein one of $R_1$ and $R_2$ is hydrogen and the other is hydrogen or $C_1$-$C_6$ alkyl, the process comprising hydrolysing a compound of formula (II)

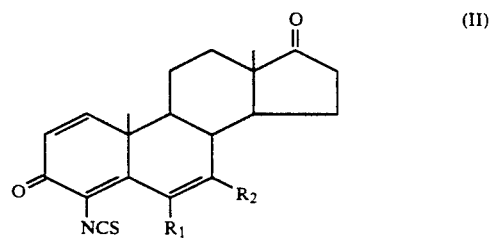

wherein $\Delta R_1$ and $R_2$ are as defined above and, if desired, salifying a compound of formula (I) or obtaining a free compound of formula (I) from a salt thereof.

In the formulae of this specification a dotted line (......) indicates a substituent in the γ-configuration, i.e. below the plane of the ring; a wedged line (◄) indicates a substituent in the β-configuration, i.e. above the plane of the ring; and a wavy line ($\sim$) indicates that a substituent may be in the α-configuration or in the β-configuration or both. Consequently, where a formula has a substituent with a wavy line bond, the formula may represent a compound having the substituent solely in the α-configuration or solely in the β-configuration, or the formula may represent a mixture of both compounds having the substituent in the α-configuration and compounds having the substituent in the β-configuration. The alkyl groups may be branched or straight chain.

A $C_1$-$C_6$ alkyl group is, preferably, a $C_1$-$C_4$ alkyl, in particular methyl, ethyl, n-propyl or tert-butyl, more preferably methyl or ethyl.

As already said, the invention includes also the pharmaceutically acceptable salts of the compounds of formula (I). Preferred salts according to the invention are the salts of the compounds of formula (I) with pharmaceutically acceptable acids, both inorganic acids such as, e.g., hydrochloric, sulfuric or phosphoric acid, and organic acids such as, e.g., citric, fumaric, maleic, malic, ascorbic, tartaric, benzoic, acetic, phenylacetic, cyclohexylacetic, 3-cyclohexylpropionic, methanesulfonic, ethanesulfonic, benzenesulfonic, p-toluene-sulfonic or p-nitrobenzenesulfonic acid.

The hydrolysis of a compound of formula (II) may be performed by treatment with a basic agent, e.g. an alkali metal hydroxide, preferably sodium or potassium hydroxide, or a salt of a quaternary ammonium base, e.g. tetrabutylammonium hydroxide, in mixtures of water and an organic solvent, e.g. dioxane, tetrahydrofurane, lower alkanols, preferably methanol or ethanol, acetone, dimethylformamide or mixtures thereof. The reaction can be performed at temperatures ranging from about 0° C. to about 50° C., preferably at room temperature. The reaction may take from about 5 minutes to about 1 hour, preferably about 30 minutes.

Conventional methods may be used for salifying a compound of formula (I) and for obtaining a free compound of formula (I) from a salt thereof.

The compounds of formula (II), which are new, can be obtained from a compound of formula (III)

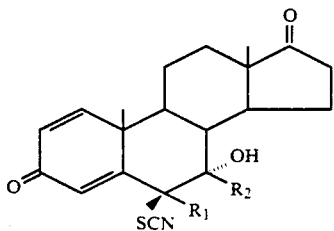

wherein $R_1$ and $R_2$ are as defined above, by heating at temperatures ranging from about 110° C. to about 135° C. in an organic solvent, e.g. dimethylformamide, dimethylacetamide, dimethylsulfoxide, diglyme or mixtures thereof, preferably dimethylformamide. The compounds of formula (III) which are new, can be obtained from a compound of formula (IV)

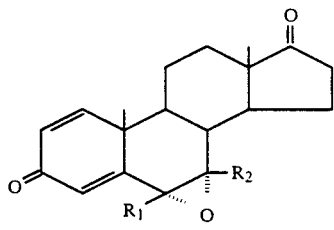

wherein $R_1$ and $R_2$ are as defined above, by treatment with an aqueous KSCN solution and an acidic agent, e.g. acetic acid, in an organic solvent, e.g. a lower alkanol, preferably methanol, at reflux temperature.

The compound of formula (IV) can be obtained from a compound of formula (V)

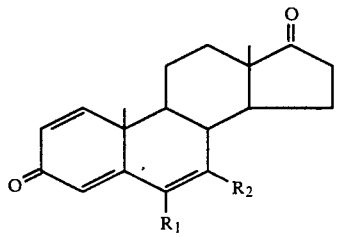

wherein $R_1$ and $R_2$ are as defined above, by epoxidation reaction with an aqueous solution of potassium peroxomonosulfate triple salt in a ketone, preferably acetone, buffered at a pH ranging from about 7 to about 8.5.

The compounds of formula (V) are either known compounds or may be obtained by known methods. For example, they may be obtained by a process comprising allylic bromination of a suitable androst-1,4-diene-3,17-dione derivative, followed by dehydrobromination, as described in U.S. Pat. No. 4,865,776.

The following examples illustrate but do not limit the present invention.

EXAMPLE 1

4-aminoandrosta-1,4,6-triene-3,17-dione

To a stirred solution of 4-isothiocyanatoandrosta-1,4-diene-3,17-dione (1.348 Kg) in dioxane (20.220 l) and water (6.158 l) is added 35% aqueous solution NaOH (0.582 l) at room temperature.

After 30 minutes 20 liters of water are added and the reaction mixture is concentrated at reduced pressure to a volume of 20 liters and then 15 liters of toluene are added.

The resulting mixture is extracted with 1.5N aqueous solution HCl (23.5 l). The cooled aqueous extract is brought to pH12 by addition of 35% aqueous solution NaOH.

The yellow precipitate is filtered off, washed with water, dried and crystallised from 95° EtOH; affording 539.75 g (45,7% yield) of the title compound, m.p. 212°–215° C.

NMR (DMSO-$d_6$, $\delta$): 0.89 (3H,s); 1.06 (3H,s); 4.87 (NH$_2$,s); 5.82 (1H,dd); 6.18 (1H,d); 6.72 (1H,dd); 7.18 (1H,d).

EXAMPLE 2

4-isothiocyanatoandrosta-1,4,6-triene-3,17-dione

The stirred solution of 7α-hydroxy-6β-thiocyanatoandrosta-1,4-diene-3,17-dione (1.528 Kg) in N,N-dimethylformamide (7.644 l) is heated to 122°–129° C. for 90 minutes.

The cooled mixture is then poured into water (53.508 l) and stirred for 30 minutes.

The resulting precipitate is filtered off, washed with water and dried in vacuo at 60° C., affording 1.363 Kg (93.93% yield) of the title compound, m.p. 146°–166° C.

NMR (CDCl$_3$, $\delta$): 0.98 (3H,s); 1.23 (3H,s); 6.19 (1H,dd); 6.35 (1H,d); 6.76 (1H,dd); 7.07 (1H,d).

EXAMPLE 3

7α-hydroxy-6β-thiocyanatoandrosta-1,4-diene-3,17-dione

To a stirred solution of 6,7α-epoxyandrosta-1,4-diene-3,17-dione (1.172 kg) in methanol (9.983 l) and 96% acetic acid (1.635 l), a solution of 1.345 Kg of KSCN in 1.503 l of water is added.

The resulting mixture is heated under reflux for 1 hour, then the methanol is removed in vacuo and the suspension is poured into 12 l of water.

After 15 minutes of stirring the solid is filtered off, washed with water and with tetrahydrofuran.

The product is dried in vacuo at 50° C., 885 g (63% yield) of the title compound are obtained; m.p. 206°–208° C.

NMR (DMSO-$d_6$, $\delta$) 0.87 (3H,s); 1.33 (3H,s); 3.95 (1H,m); 4.56 (1H,d); 5.76 (1H,d); 6.16 (1H,dd); 6.29 (1H,d); 7.23 (1H,d).

EXAMPLE 4

6,7α-epoxyandrosta-1,4-diene-3,17-dione

To a well stirred and cooled mixture (5°–10° C.) of androsta-1,4,6-triene-3,17-dione (725 g) and acetone (21.750 l), buffered (pH8, 0.125M phosphate buffer), is added dropwise during two hours a fresh solution of potassium peroxomonosulfate triple salt (2.9 Kg) in water (12.686 l). During the addition the pH is monitored and kept constant by using a pH-stat (4% NaOH aqueous solution).

The mixture is allowed to stand at 5°–10° C. for 15 minutes with stirring and then an aqueous solution of saturated sodium metabisulfite (250 ml) is added dropwise.

The acetone is removed in vacuo and the aqueous mixture is cooled to 20° C. and stirred for 15 minutes.

The reslting precipitate is filtered off, washed several times with water and dried in vacuo at 50° C., affording 560 g of the title compound (73% yield); m.p. 182°–194° C.

NMR (CDCL$_3$,δ): 0.96 (3H,s); 1.55 (3H,s); 3.44 (1H,dd); 3.67 (1H,d); 6.22 (1H,dd); 6.47 (1H,d); 6.97 (1H,d):

EXAMPLE 5

4-aminoandrosta-1,4,6-triene-3,17-dione hydrochloride

A solution of 0.5 g of 4-aminoandrosta-1,4,6-triene-3,17-dione in 20 ml of ethanol is treated with 16.7 ml of 0.1N HCl aqueous solution. The yellow solution is then treated with 0.02 of carbon, filtered and the alcohol is distilled at reduce pressure. The resulting aqueous solution is lyophilysed to give 0.54 g of dry title compound as slightly yellow power.

We claim:

1. A process for the preparation of 4-amino androstanedione derivatives having the following formula (I), and the pharmaceutically acceptable salts thereof,

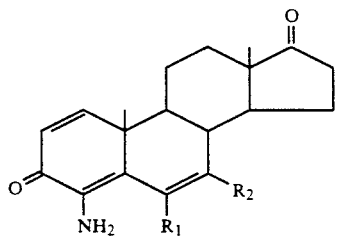

(I)

wherein Δone of R$_1$ and R$_2$ is hydrogen and the other is hydrogen or C$_1$–C$_6$ alkyl, the process comprising hydrolysing a compound of formula (II)

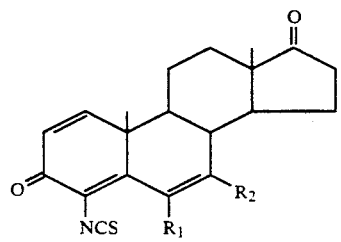

(II)

wherein ΔR$_1$ and R$_2$ are as defined above and optionally salifying a compound of formula (I) or obtaining a free compound of formula (I) from a salt thereof.

2. A process according to claim 1, wherein the compound of formula (II) is obtained by heating a compound of formula (III)

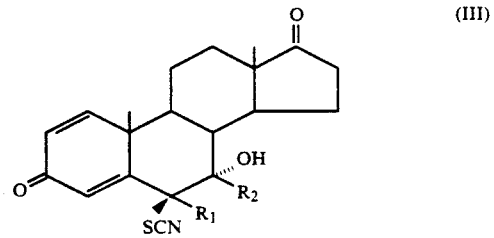

(III)

wherein ΔR$_1$ and R$_2$ are as defined as in claim 1, at temperatures ranging from about 110° C. to about 135° C. in an organic solvent.

3. A process according to claim 2, wherein the compound of formula (III) is obtained by treating a compound of formula (IV)

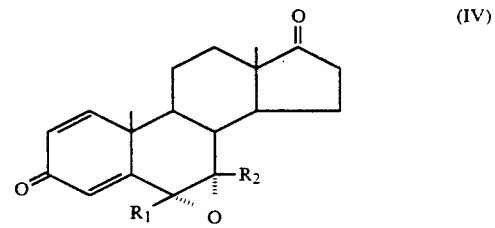

(IV)

wherein ΔR$_1$ and R$_2$ are as defined in claim 1, with an aqueous KSCN solution and an acidic agent in an organic solvent, at the reflux temperature.

4. A process according to claim 3, wherein the compound of formula (IV) is obtained by epoxidating a compound of formula (V)

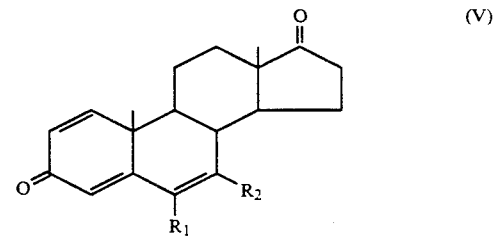

(V)

wherein R$_1$ and R$_2$ are as defined in claim 1, with an aqueous solution of potassium peroxomonosulfate triple salt in a ketone buffered at a pH ranging from about 7 to about 8.5.

5. A compound of formula (II)

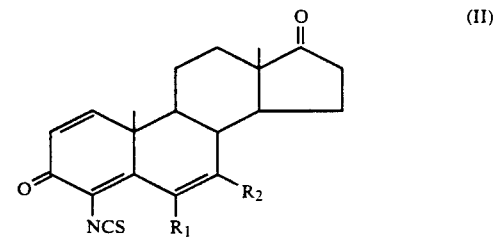

(II)

wherein Δone of R$_1$ and R$_2$ is hydrogen and the other is hydrogen or C$_1$–C$_6$ alkyl.

6. A compound of formula (III)

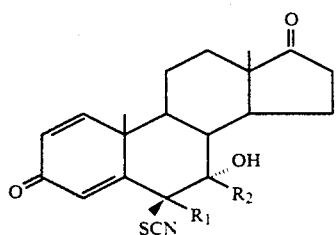
(III)
wherein one of $R_1$ and $R_2$ is hydrogen and the other is hydrogen or $C_1$–$C_6$ alkyl.
* * * * *

UNITED STATES PATENT AND TRADEMARK OFFICE
CERTIFICATE OF CORRECTION

PATENT NO. : 5,241,090
DATED : AUGUST 31, 1993
INVENTOR(S) : FABRIZIO ORZI ET AL

It is certified that error appears in the above-indentified patent and that said Letters Patent is hereby corrected as shown below:

Column 2, line 40, after "wherein", delete "Δ".

Column 5, line 52, after "wherein", delete "Δ";
         line 66, after "wherein", delete "Δ".

Column 6, line 15, after "wherein", delete "Δ";
         line 32, after "wherein", delete "Δ";
         line 66, after "wherein", delete "Δ".

Signed and Sealed this

Thirteenth Day of September, 1994

Attest:

BRUCE LEHMAN

Attesting Officer     Commissioner of Patents and Trademarks